(12) United States Patent
Drake

(10) Patent No.: US 10,137,219 B2
(45) Date of Patent: Nov. 27, 2018

(54) COHERENT BLOOD COAGULATION STRUCTURE OF WATER-INSOLUBLE CHITOSAN AND WATER-DISPERSIBLE STARCH COATING

(71) Applicant: James F. Drake, Minneapolis, MN (US)

(72) Inventor: James F. Drake, Minneapolis, MN (US)

( * ) Notice: Subject to any disclaimer, the term of this patent is extended or adjusted under 35 U.S.C. 154(b) by 1132 days.

(21) Appl. No.: 14/451,417

(22) Filed: Aug. 4, 2014

(65) Prior Publication Data

US 2016/0030623 A1     Feb. 4, 2016

(51) Int. Cl.

| | |
|---|---|
| *A61L 15/28* | (2006.01) |
| *A61L 15/42* | (2006.01) |
| *B32B 5/02* | (2006.01) |
| *B32B 5/14* | (2006.01) |
| *B32B 5/22* | (2006.01) |
| *B32B 5/26* | (2006.01) |
| *B32B 9/02* | (2006.01) |

(Continued)

(52) U.S. Cl.
CPC .............. *A61L 15/28* (2013.01); *A61L 15/42* (2013.01); *A61L 15/425* (2013.01); *B32B 5/02* (2013.01); *B32B 5/022* (2013.01); *B32B 5/145* (2013.01); *B32B 5/22* (2013.01); *B32B 5/26* (2013.01); *B32B 9/02* (2013.01); *B32B 9/047* (2013.01); *B32B 27/12* (2013.01); *B32B 27/283* (2013.01); *B32B 27/32* (2013.01); *B32B 27/322* (2013.01); *B32B 27/40* (2013.01); *A61L 2400/04* (2013.01); *B32B 2255/02* (2013.01); *B32B 2255/26* (2013.01); *B32B 2262/06* (2013.01); *B32B 2307/726* (2013.01); *B32B 2307/728* (2013.01); *B32B 2535/00* (2013.01)

(58) Field of Classification Search
CPC ........ A61L 15/28; A61L 15/42; A61L 15/425; A61L 2400/04; B32B 5/02; B32B 5/022; B32B 5/145; B32B 5/22; B32B 5/26; B32B 9/02; B32B 9/047; B32B 27/12; B32B 27/283; B32B 27/32; B32B 27/322; B32B 27/40; B32B 2255/02; B32B 2400/26; B32B 2262/06; B32B 2307/726; B32B 2307/728; B32B 2535/00

See application file for complete search history.

(56) References Cited

U.S. PATENT DOCUMENTS 3,620,218 A    11/1971   Schmitt et al.
3,937,223 A    2/1976    Roth
(Continued)

*Primary Examiner* — Jacqueline Stephens
(74) *Attorney, Agent, or Firm* — Mark A. Litman & Assoc, P.A.

(57) ABSTRACT

An absorbent layer for moderating blood flow from a wound has a non-woven fabric layer of water-insoluble chitosan fibers having a coating of water-absorbent starch on at least one face of the fabric layer. The coating of water-absorbent starch penetrates into the fabric layer from a first surface over the chitosan fibers to a depth of at least 25% of the fabric layer of chitosan fibers. The chitosan fibers have average diameters of from 5 to 30 micrometers. The average weight of starch/chitosan may decrease from the first surface from which the starch has penetrated into the fabric to the depth of at least 50% of the fabric layer. The starch may be modified to include hydrophilic groups into or onto molecular chains of the starch.

26 Claims, 7 Drawing Sheets

SEM, top view, of nonwoven matrix with coating, 100 X magnification

(51) Int. Cl.
 *B32B 9/04* (2006.01)
 *B32B 27/12* (2006.01)
 *B32B 27/28* (2006.01)
 *B32B 27/32* (2006.01)
 *B32B 27/40* (2006.01)

(56) References Cited

U.S. PATENT DOCUMENTS

| | | |
|---|---|---|
| 6,197,322 B1 * | 3/2001 | Dutkiewicz ............ A01N 25/34 424/404 |
| 7,101,862 B2 | 9/2006 | Cochrum et al. |
| 8,063,264 B2 | 11/2011 | Spearman et al. |
| 8,575,132 B2 | 11/2013 | Ji et al. |
| 8,703,176 B2 | 4/2014 | Zhu et al. |
| 2003/0220048 A1 * | 11/2003 | Toro ................... A61F 13/51462 450/57 |
| 2005/0137512 A1 * | 6/2005 | Campbell ........... A61F 13/0276 602/41 |
| 2005/0240137 A1 * | 10/2005 | Zhu .................... A61B 17/0057 602/56 |
| 2009/0287176 A1 * | 11/2009 | Carlucci ................ A61L 15/28 604/375 |
| 2013/0123213 A1 * | 5/2013 | Ji ......................... A61K 31/718 514/55 |

* cited by examiner

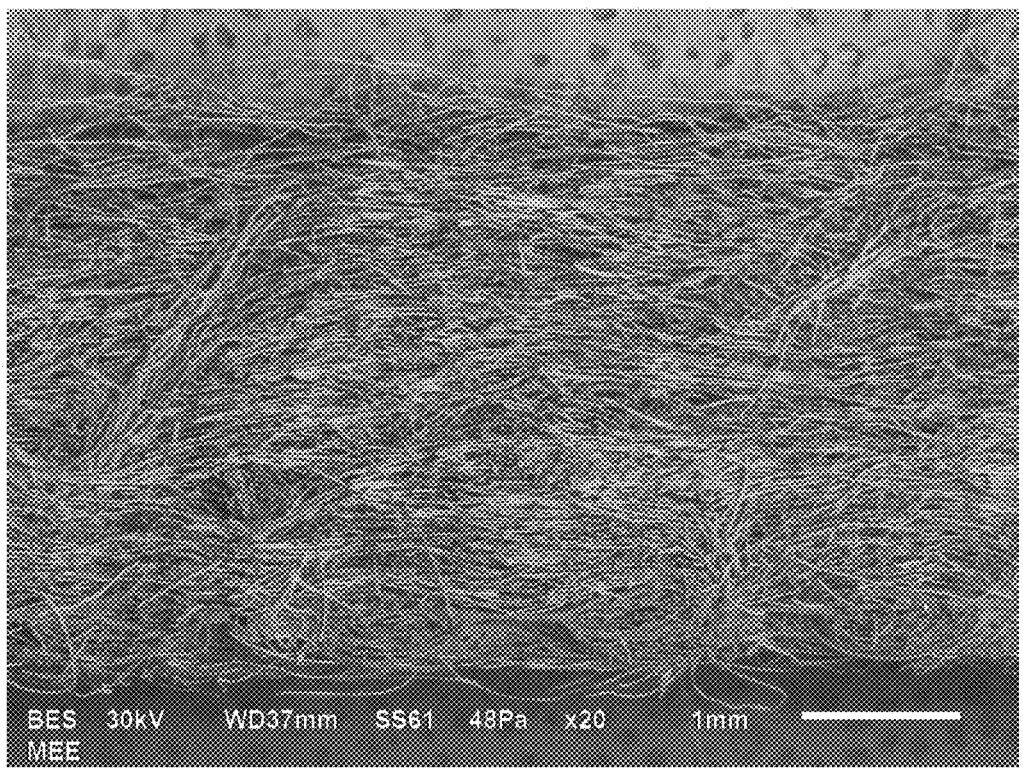
FIGURE 1A, SEM, side or edge view, of nonwoven matrix without AMP at 20X magnification
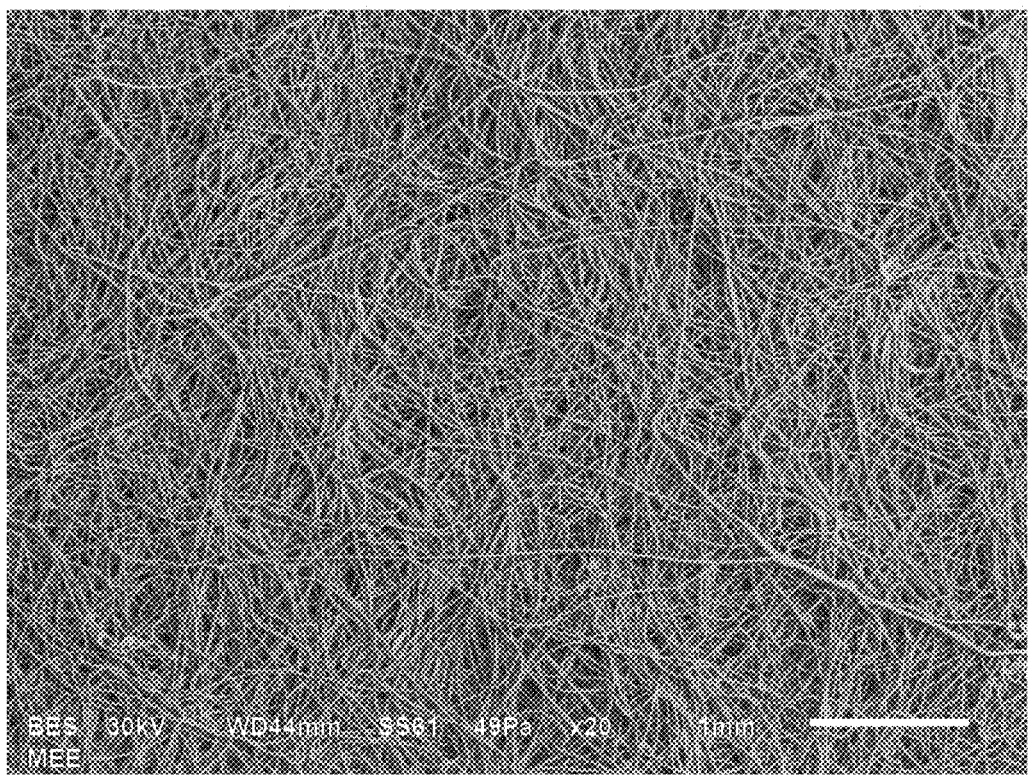
FIGURE 1B – SEM, top view, of nonwoven matrix without AMP at 20 X magnification

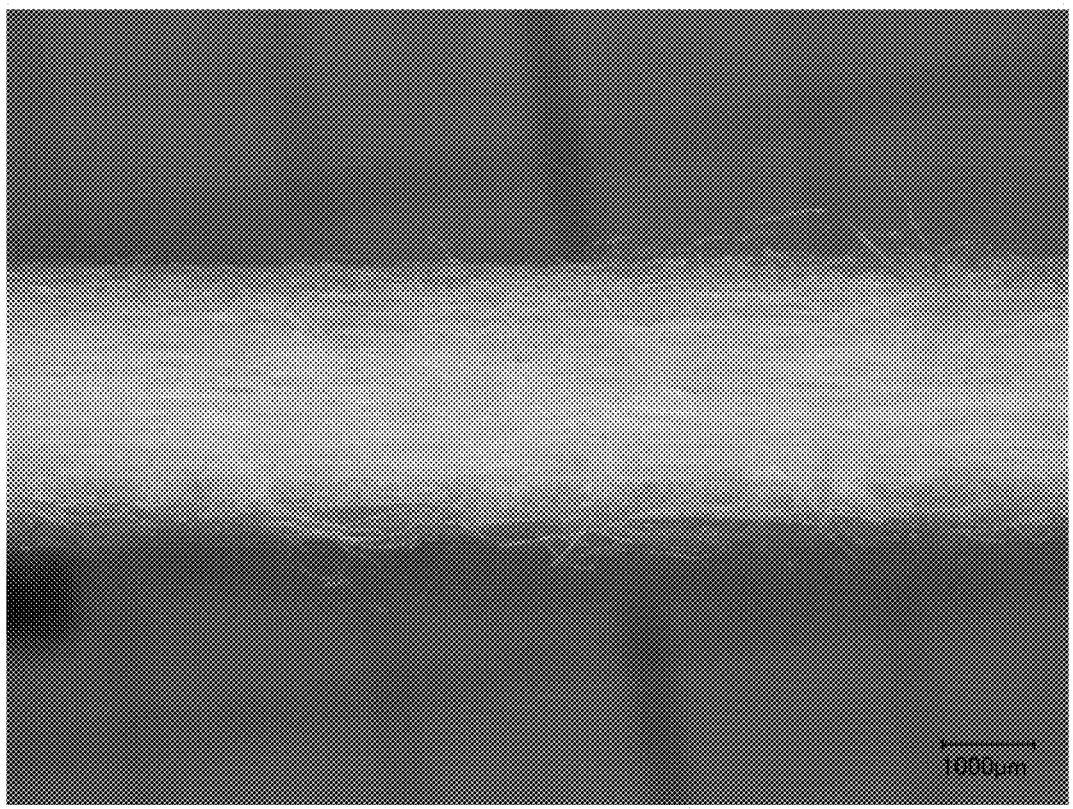
FIGURE 2A — LM, side or edge view, nonwoven matrix without AMP at 25 X magnification
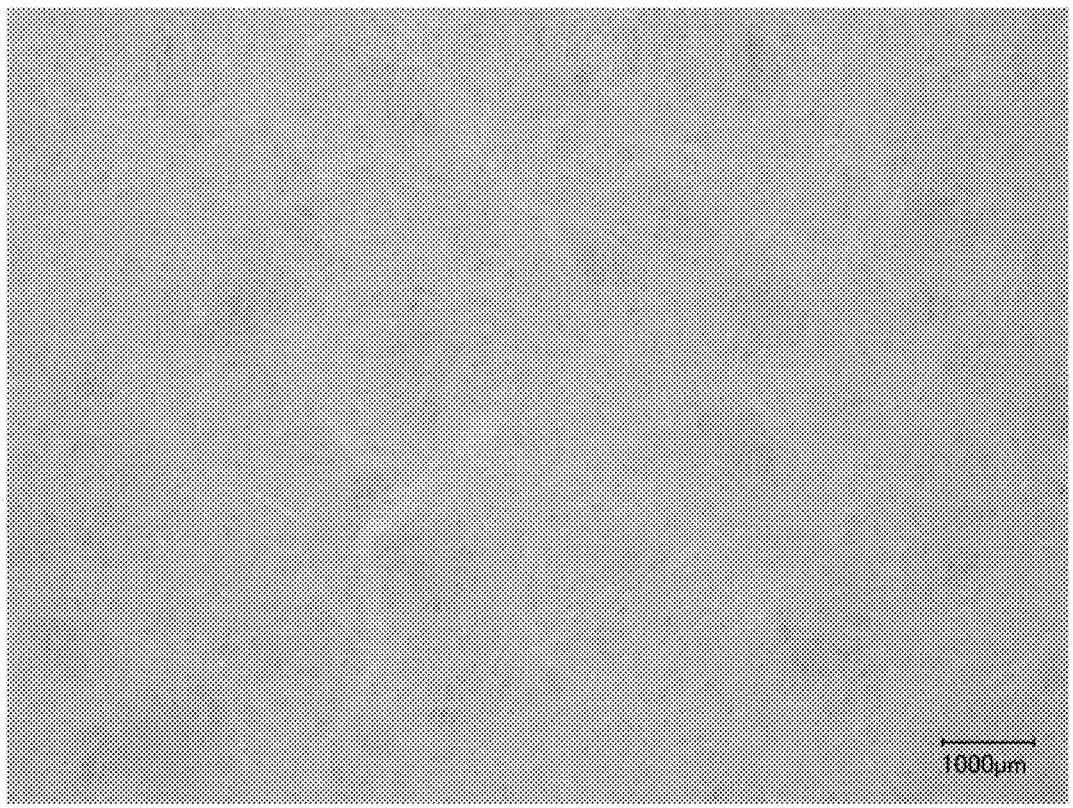
FIGURE 2B — LM, top view, nonwoven matrix without AMP at 25 X magnification

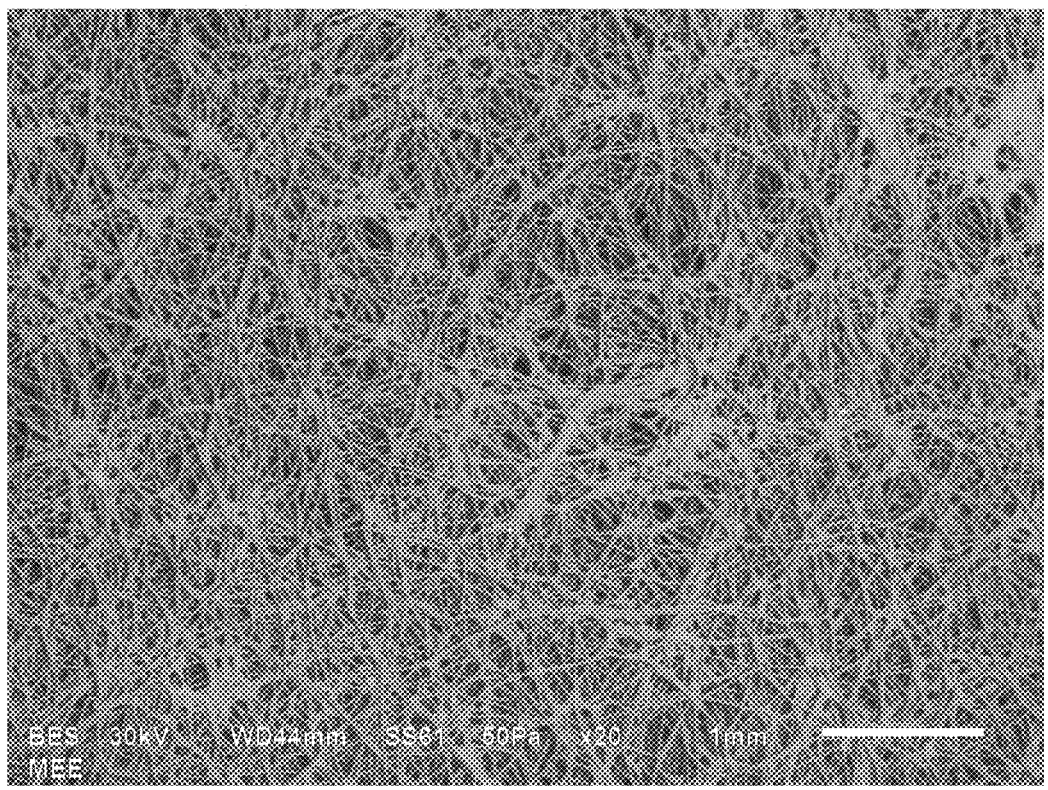
FIGURE 3A – SEM, top view, of nonwoven matrix with coating, 20 X magnification
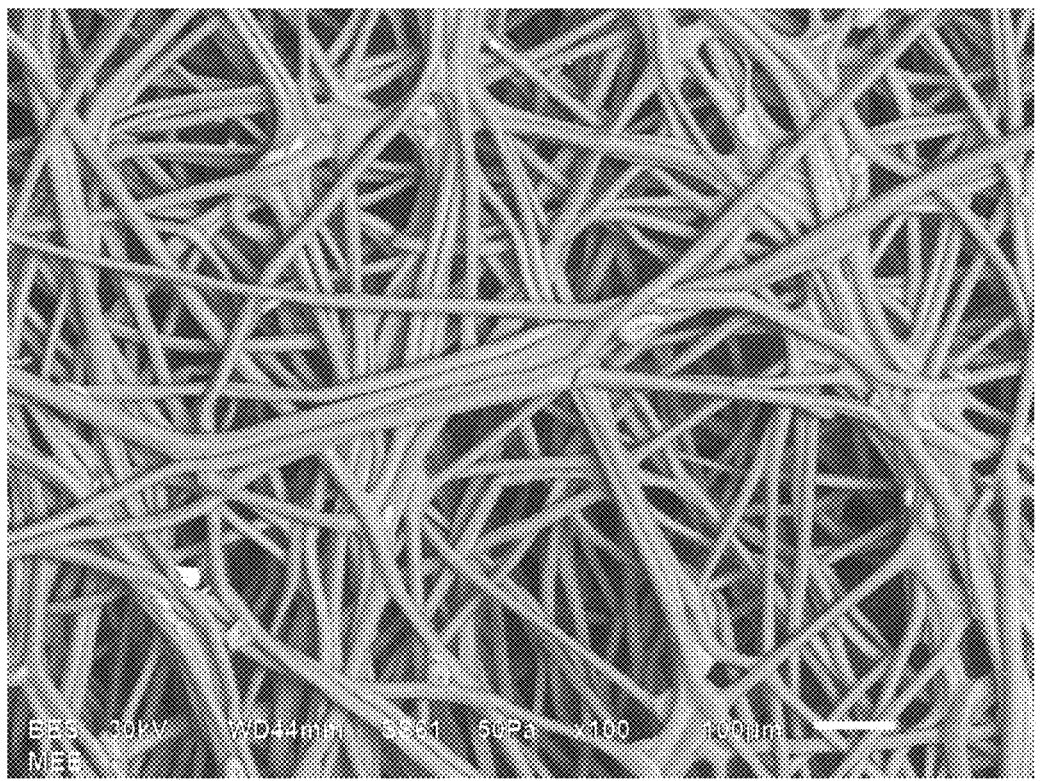
FIGURE 3B – SEM, top view, of nonwoven matrix with coating, 100 X magnification

FIGURE 4A – LM, top view, of the nonwoven matrix with coating at 25 X magnification
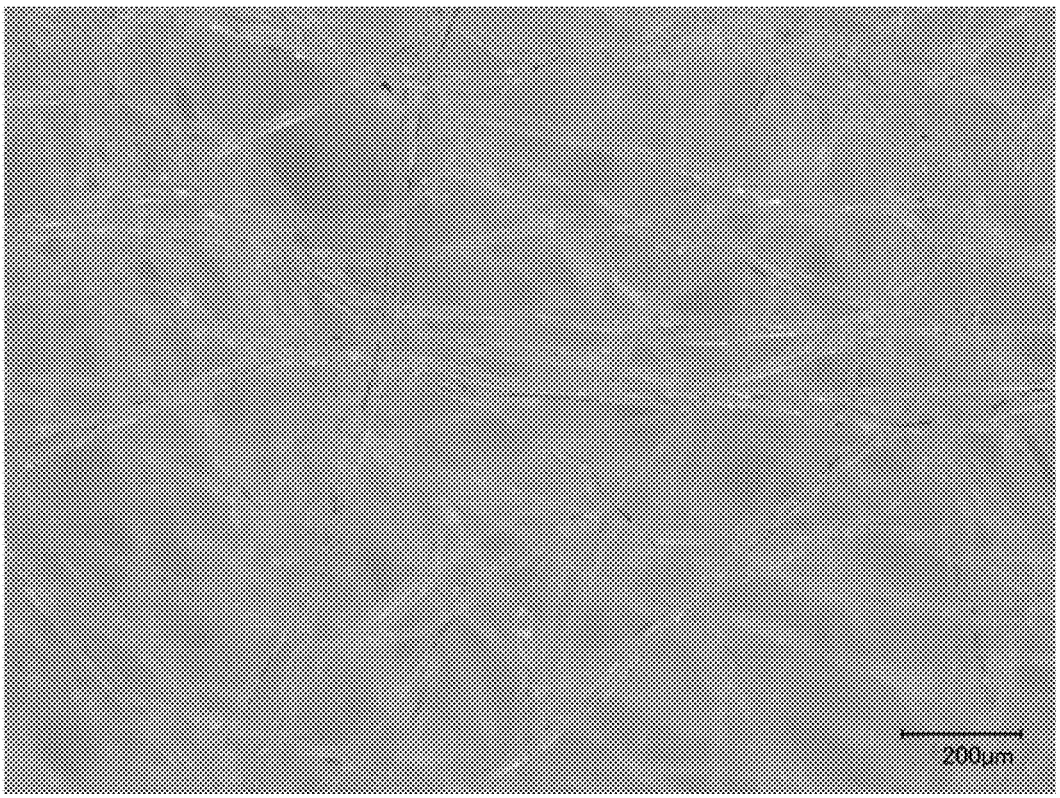
FIGURE 4B – LM, top view, of the nonwoven matrix with coating at 67 X magnification

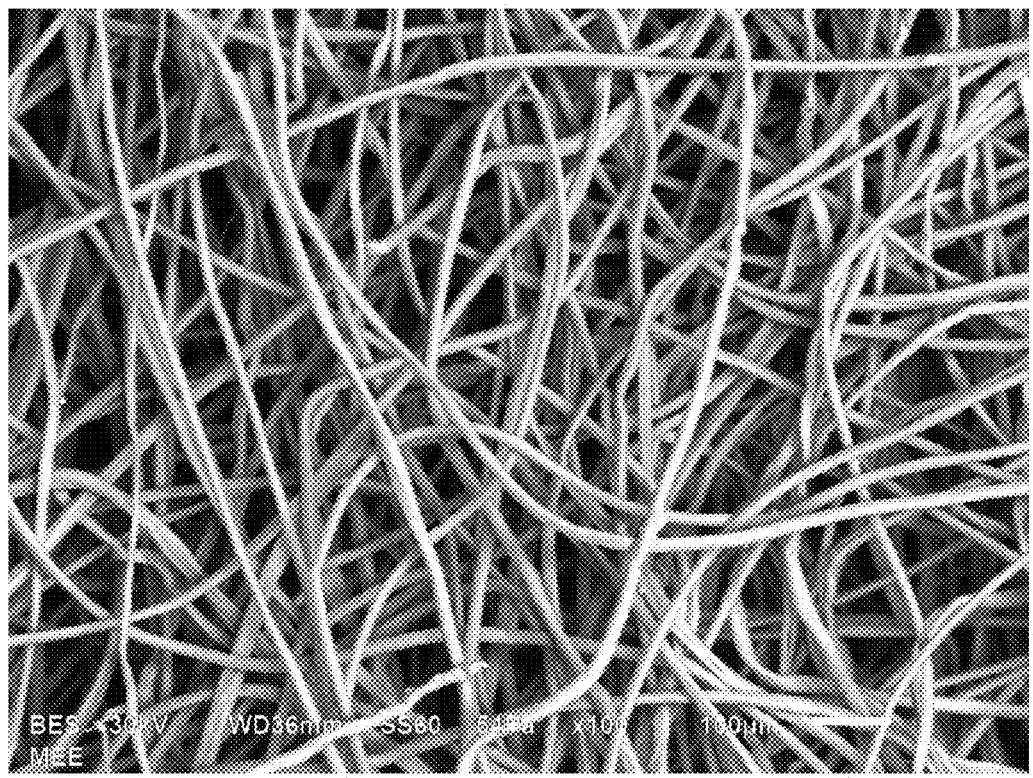
Figure 5A, SEM of machine coated Chitosan-STF. Magnification is 100x
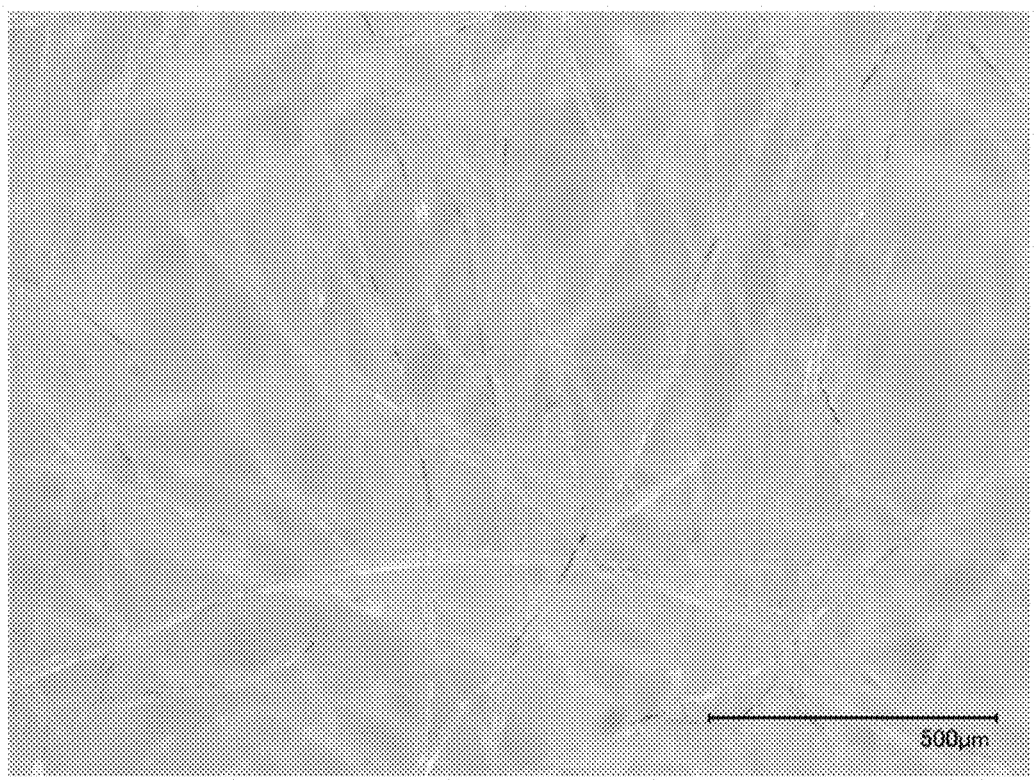
Figure 5B, LM of machine coated Chitosan-STF. Magnification is 67X

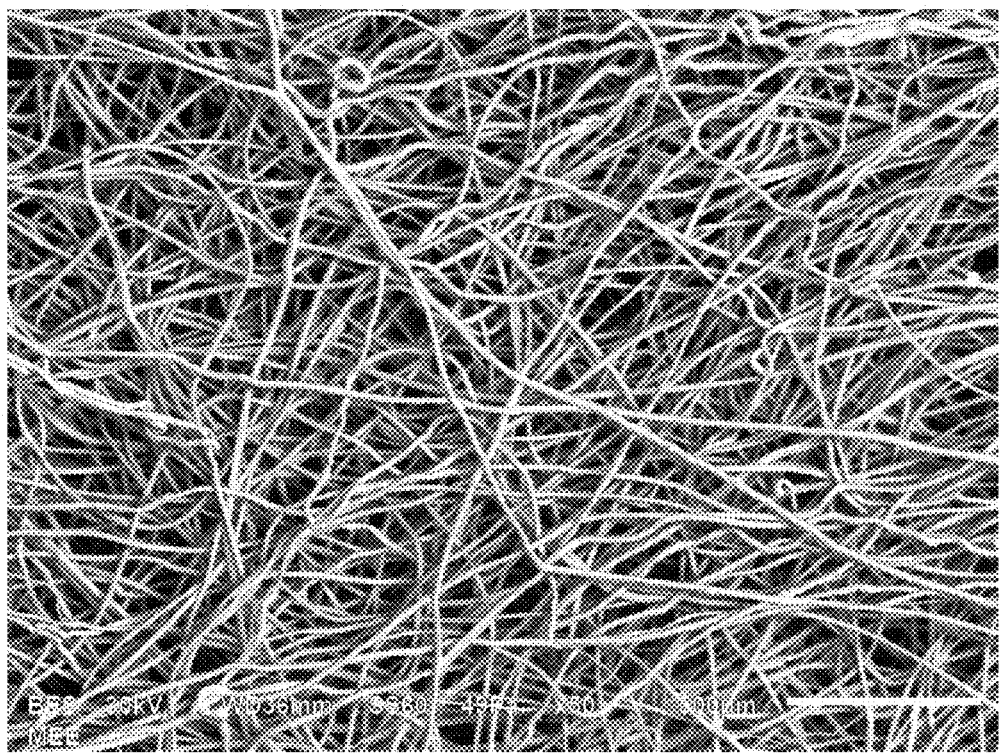
Figure 6A, SEM of machine coated Chitosan-STF. Magnification is 50X
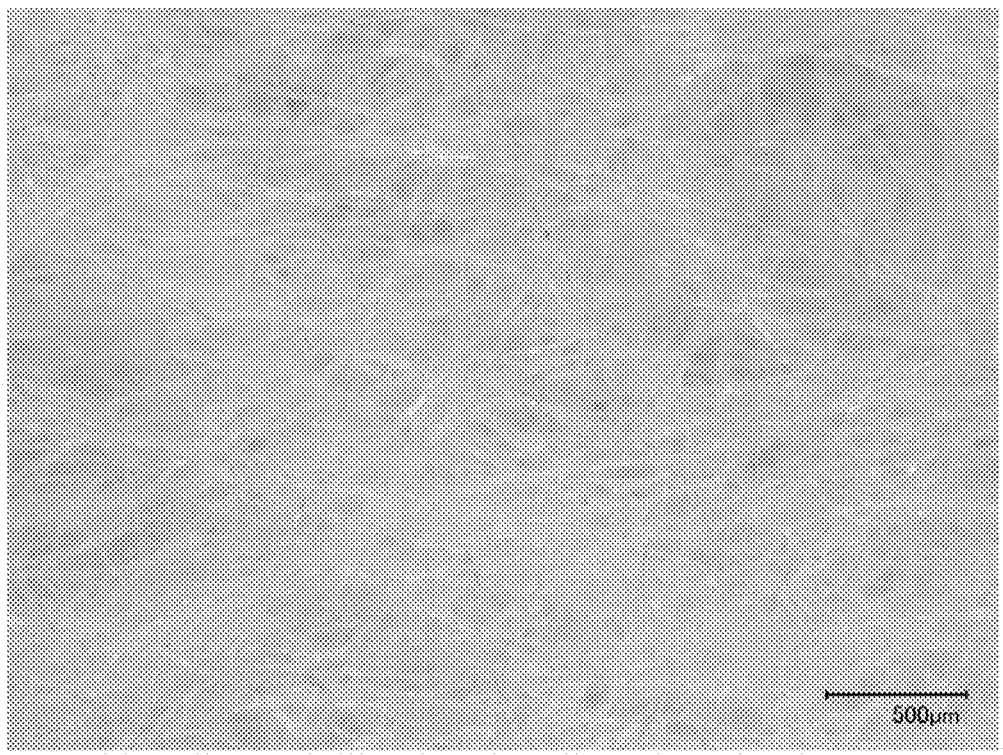
Figure 6B, LM of machine coated Chitosan –STF. Magnification is 33X

COHERENT BLOOD COAGULATION STRUCTURE OF WATER-INSOLUBLE CHITOSAN AND WATER-DISPERSIBLE STARCH COATING

BACKGROUND OF THE ART

1. Field of the Invention

The present invention relates to the field of blood control at wound sites and coagulation of blood within a structure provided at a wound site.

2. Background of the Art

It has been recognized in the prior art that it is desirable to stop bleeding by applying materials to the wound or tissue which initiate or enhance blood coagulation. Such materials have included collagen, gelatin, oxidized regenerated cellulose, kaolin, polysaccharides such as starch or chitosan, liquid glues (cyanoacrylate adhesives, gelatinous glues, UV curable polymers, etc.) to name a few. Other materials which are made from human or animal blood components such as thrombin, albumin and fibrinogen have been used but carry the risk of virus infection and are expensive to manufacture.

One method used to reduce bleeding involves initiating or accelerate blood clotting by applying hygroscopic porous particles directly to a wound. In this method the porous particles absorb the water from blood allowing the natural fibrinogens within the blood to coagulate, which results in a blood clot. The pore size of such particles should be such that water is able to be readily absorbed by the particles, but the clot forming blood components (thrombin, fibrinogen, fibrin, platelets, etc.) are not. The size of the pores, therefore, should be less than 1 micrometer (1,000 nm) and preferably less than 0.1 micrometer (100 nm). The particles may be made of many different materials, although it is preferable that the materials be biocompatible and eventually absorbed by the body. Another method in U.S. Pat. No. 4,822,349 (Hursey) describes the use of zeolites, or molecular sieves, for accelerating clotting. The zeolites are used in a particle form either as a powder poured onto or into a wound, or embedded in a wound dressing. However, while effective at adsorbing water from the blood and stopping bleeding, this method suffers from several problems. Zeolites are inorganic and are not readily absorbed by the body. This creates significant difficulties in caring for the wound once the bleeding is stopped. The zeolite particles, which have been placed in the wound, must be debrided or scraped out of the wound once the bleeding has stopped. This can be painful for the trauma victim and require multiple surgical debridements. There is also an exothermic reaction when water is adsorbed into zeolites that can cause the temperatures at the wound site to reach 40° C. to 50° C. or higher which can damage tissue and irritate the patient. Also a significant number of people can have allergic reactions to the zeolites. Another major concern is that the loose zeolite particles can become entrained in a blood vessel where they will continue to promote formation of clots. These small clots, which can then circulate in the blood system, can potentially cause embolisms, strokes, or other clot related problems. U.S. Pat. No. 6,060,461 (Drake) describes the use of particles made of porous materials from within the classes of polysaccharides, cellulosics, polymers (natural and synthetic), inorganic oxides, ceramics, zeolites, glasses, metals and composites.

Polysaccharides are preferred because of their ready availability and modest cost. They are widely known to be biocompatible and are readily absorbed by the body over time. Polysaccharides can be provided as starch, cellulose, and even chitosan. Chitosan based wound dressings provided under the trade names SoftSeal®-STF chitosan, Celox™ chitosan, "HemCon®" chitosan are all products based upon chitosan chemistry. The chitosan is derived from chitin particles obtained from crustaceans such as crab or shrimp. The particles can be applied in a powder form directly to the wound, or held in place on the wound. However, powders are difficult to apply, especially to wounds in which blood is flowing since the powders can be washed away with the flowing blood before clotting can be initiated.

A solution to problem of the powders washing away is described in the Hursey and Drake patents wherein they embed or attach the powders to a wound dressing. The wound dressing can take the form of a sheet or film in which the particles are adhered to or to the surface of fibers which make up woven or non-woven gauze-like fabric or sheet. The particles can also be interspersed with fibers, filaments or other particles in a self-supporting structure, entangled within the fibrous elements of a net, web, fabric or sheet. However, both the biocompatible particles and the zeolite particles suffer the same problem in that they can become entrained in the blood vessels and cause clotting related problems in the blood vessels. While both of the Hursey and Drake patents describe the use of a dressing with the particles embedded or attached to a dressing for ease of application, there still exists the danger of the particles shedding from dressing and becoming entrained in the blood vessel and causing clotting within a blood vessel. In addition, the use of a dressing made of one material combined with the particles made of a different material increases problems of biocompatibility and absorption. It also increases the complexity of manufacturing and consequently manufacturing costs. U.S. Pat. No. 3,620,218 (Schmitt) discloses a felt made of polyglycolic acid fibers which may be used as a hemostat. However, the felted fibers can float from a bleeding surface and are generally too porous.

U.S. Pat. No. 3,937,223 (Roth) discloses an asserted improvement upon U.S. Pat. No. 3,620,218 by compaction of the felt on at least one side to provide strength and rigidity to the felt as well as providing a smoother surface which can be drawn into close conformity to the wound and thus reduce pockets in the felt where blood or other fluids can accumulate. Roth uses filaments of about 0.5 to 12 deniers per filament (approximately 7 um to 34 um) and, conveniently, 2 to 6 deniers (approximately 14 um to 24 um) per filament. These fibers are quite large and stiff which creates large pores when made into a felt. To reduce the large pores one compresses the felt to smoothen the surface of the felt and to press the filaments closer together to create smaller pores between the fibers and thereby enhance hemostatic properties of the felt. However, even after compaction this technique suffers from the large open regions or void volume. When the filaments are compressed together, the void volume, or amount of open area between fibers, is greatly reduced. The amount of open area between fibers is important as the open area allows water to be wicked between the fibers, leaving behind platelets and other clotting agents, thus initiating the clotting process. The void volumes in compressed and calendared felts are typically less than 70% and usually less than 50%. The low void volumes in the felt reduces the hemostatic effectiveness of the compressed felts since the wicking of the water from the blood is a function of the surface area of fibers in contact with the blood and the capillary effect created by the pore size as well as the number of pores in the surface of the media. In addition, to the less than optimal hemostatic properties, the fibers in the felt which have not been compacted or embossed are not bonded to the other fibers.

U.S. Pat. No. 8,063,264 (Spearman) discloses a wound dressing and a method for enhancing the clotting comprising a plurality of hydrophilic microfibers bonded to each other to form a mat with the plurality of microfibers having a pore size sufficiently small to inhibit wicking platelets from a wound into the microfibers so that when applied to a wound the blood coagulates and the microfibers remain external to the wound. Another example of fiber matrix wound dressing for hemostasis is U.S. Pat. No. 8,703,176 (Zhu).

U.S. Pat. No. 7,101,862 (Cochrum) provides hemostatic compositions useful to promote hemostasis at active bleeding wound sites. The hemostatic compositions typically include an article containing cellulose, e.g., cotton gauze, and a polysaccharide covalently linked to the cellulose, or a polysaccharide ionically cross-linked and in association with the article. Methods of making and using the hemostatic compositions are also provided.

U.S. Pat. No. 8,575,132 (Ji) describes a modified starch material for biocompatible hemostasis, biocompatible adhesion prevention, tissue healing promotion, absorbable surgical wound sealing and tissue bonding, when applied as a biocompatible modified starch to the tissue of animals. The modified starch material produces hemostasis, reduces bleeding of the wound, extravasation of blood and tissue exudation, preserves the wound surface or the wound in relative wetness or dryness, inhibits the growth of bacteria and inflammatory response, minimizes tissue inflammation, and relieves patient pain. Any excess modified starch not involved in hemostatic activity is readily dissolved and rinsed away through saline irrigation during operation. After treatment of surgical wounds, combat wounds, trauma and emergency wounds, the modified starch hemostatic material is rapidly absorbed by the body without the complications associated with gauze and bandage removal.

All referenced cited herein are incorporated by reference in their entirety.

SUMMARY OF THE INVENTION

An absorbent layer for controlling or moderating blood flow from a wound has a non-woven fabric layer of water-insoluble chitosan fibers having a coating of water-absorbent starch on at least one face of the fabric layer. The coating of water-absorbent starch penetrates into the fabric layer from a first surface over the chitosan fibers to a depth of at least 25% of the fabric layer of chitosan fibers. The chitosan fibers have average diameters of from 5 to 30 micrometers. The average weight of starch/chitosan may decrease from the first surface from which the starch has penetrated into the fabric to the depth of at least 50% of the fabric layer. The starch may be modified to include hydrophilic groups into or onto molecular chains of the starch.

BRIEF DESCRIPTION OF THE FIGURES

FIG. 1A is a scanning electron micrograph (SEM) of a nonwoven chitosan fiber matrix without any added starch. The view is a top view of the fiber mat. The magnification is 20×.

FIG. 1B is an electron micrograph (SEM) of a nonwoven chitosan fiber matrix without any added starch. The view is a top view of the fiber mat. The magnification is 20×.

FIG. 2A is a light micrograph (LM) of nonwoven chitosan fiber matrix without any added starch. The view is an edge view of the fiber mat. The magnification is 25×.

FIG. 2B is a light micrograph (LM) of nonwoven chitosan fiber matrix without any added starch. The view is a top view of the fiber mat. The magnification is 25×.

FIG. 3A is a scanning electron micrograph (SEM) of a nonwoven chitosan fiber matrix with an additional coating of starch. The view is a top view. The magnification is 20×.

FIG. 3B is a scanning electron micrograph (SEM) of a nonwoven chitosan fiber matrix with an additional coating of starch. The view is a top view. The magnification is 100×.

FIG. 4A is a light micrograph (LM) of nonwoven chitosan fiber matrix with an additional coating of starch. The view is a top view of the fiber mat. The magnification is 25×.

FIG. 4B is a light micrograph (LM) of nonwoven chitosan fiber matrix with an additional coating of starch. The view is a top view of the fiber mat. The magnification is 67×. The image shows the transparency/translucency to white light of the modified starch coating and transparency/translucency to white light of the underlying chitosan fabric substrate.

FIG. 5 is an illustrative rendition and is not intended to be a limiting description of distribution of materials, thicknesses and rheology of layers, it can be seen that in Zone 1, there is a heavier thickness 106 of the starch coating 106a. In Zone 2, there is a thinner coating 108 of the starch coating 106a. In Zone 3, there tends to be a more discontinuous coating 110 of the starch coating 106a. In Zone 4, there is essentially no starch coating 106a in this rendition. There are open volumes 112 between the coated 106a chitosan fibrous elements 104 within the matrix 100. The distribution is illustrative of how materials are likely to be distributed from a single side (through surface 102) application of the starch coating 106a. Different methods of application (e.g., two-side application, dipping, pressure-coating, spray coating, meniscus coating and the like) will create varying patterns if starch distribution within the matrix 100. For example, with two side coating application of the starch, a complete cross-section distribution might look more like a mirror image of Zone 1, Zone 2, Zone 2 again and Zone 1 again (in order) so that there is a relatively continuous, though varying in thickness, coating of starch across the entire thickness of the matrix. It might also be possible to have mirror cross-sections of a) Zone 1, Zone 2, Zone 3m Zone 2, Zone 1, or b) Zone 1, Zone 2, Zone 3, Zone 4, Zone 3, Zone 2 and Zone 1, Not only the thickness of the starch coating 106 may vary across the thickness of the fabric, but also the coating weight per volume will vary and the coating weight variations (in a two-side coated matrix) may be different from one surface versus the other surface.

FIG. 5A is an SEM of Chitosan-STF fibers machine coated with starch. The magnification is 100×.

FIG. 5B is a LM of Chitosan-STF fibers machine coated with starch. The magnification is 67×.

FIG. 6A is an SEM of Chitosan-STF fibers machine coated with starch The magnification is 50×.

FIG. 6B is an LM of Chitosan-STF fibers machine coated with starch. Magnification is 33×.

DETAILED DESCRIPTION OF THE INVENTION

Figure 5:
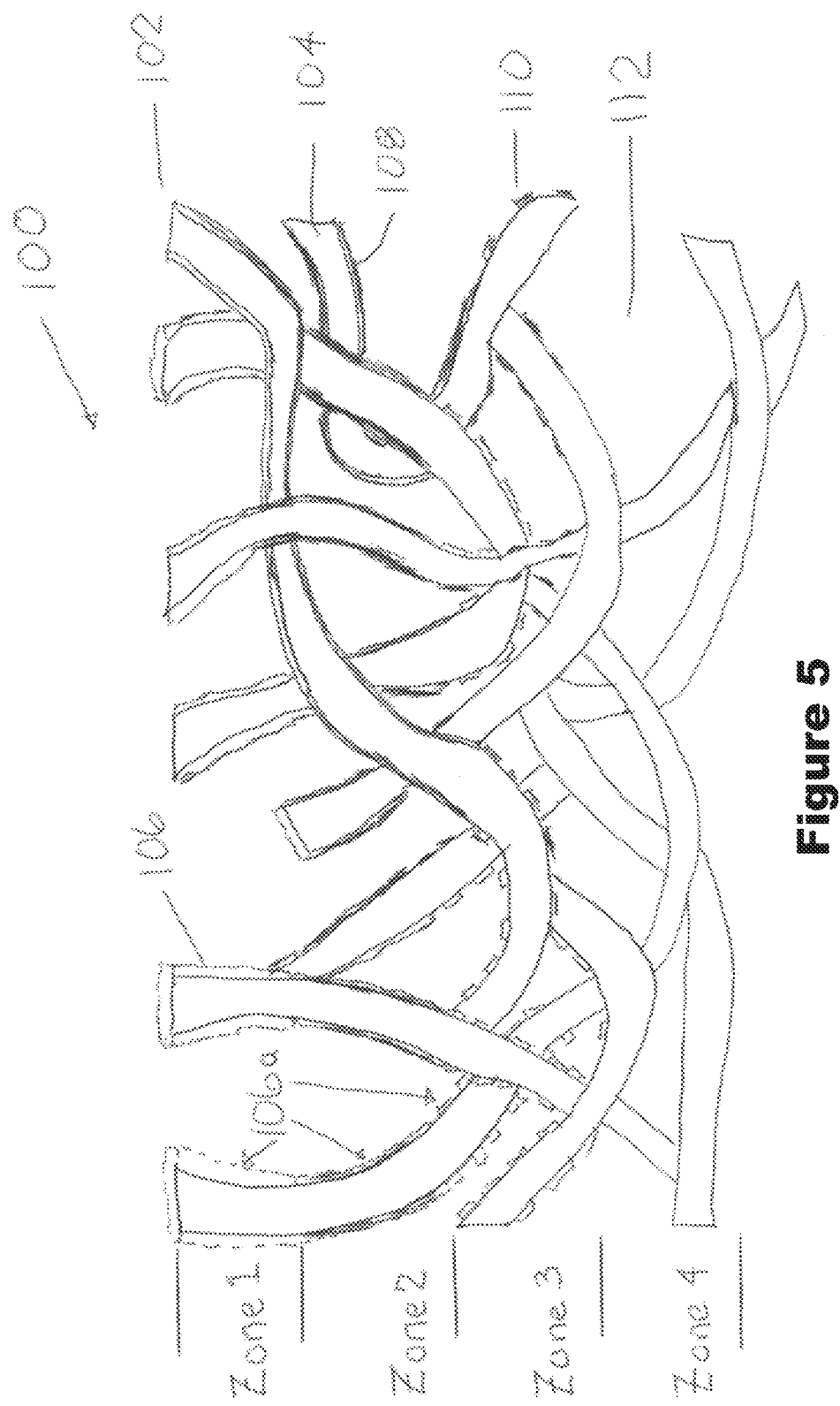
FIG. 5 is a schematic representation of a cutaway side view of the chitosan fiber matrix similar to that of FIGS. 3A and 3B emphasizing distribution of the starch layer 106a from one surface 102 into the non-woven chitosan 104. Remembering that this

An absorbent layer has a non-woven fabric layer of water-insoluble chitosan fibers having a coating of water-absorbent starch on at least one face of the fabric layer. The coating of water-absorbent starch may penetrate into the fabric layer from a first surface over the chitosan fibers to a depth of at least 25% of the fabric layer of chitosan fibers towards a second surface. The chitosan fibers may have average diameters (not lengths) of from 5 to 30 micrometers, 8 to 25 micrometers or 10 to 20 micrometers. The fibers may have aspect ratios of from 1.5 to 50 (or more if continuous fibers). The average weight of starch/chitosan decreases from the first surface from which the starch has penetrated into the fabric to the depth of at least 50% of the fabric layer. The decrease may be graded (e.g., nominally from a 60/40 starch to chitosan at the surface region (e.g., the first 10% of depth) to a nominal 10/90 ratio). The gradation may be straight-line linear or slower drop=off or faster drop-off depending upon methodology of applying the starch and/or intentional design. The coating may be on only one side of the layer or may be applied from both sides to provide an asymmetric distribution or symmetric distribution, respectively.

The starch component of the layer, as described in greater detail herein may be a starch that has been modified to include hydrophilic groups attached onto molecular chains of the starch. The layer may be carried on a structural support secured to the second surface of the layer.

A method is provided herein of mediating blood flow from a wound by applying the first surface of a layer according to the present technology against the wound from which blood is flowing and clotting blood from the wound.

Chitin is recovered from crab shells by treatment with acid to remove the minerals and with alkali to remove protein. After these treatments, purified chitin remains as thin, white sheets that are further processed into chitosan. Chitosan is made by heating purified chitin with strong alkali to remove some of the acetyl groups from the polymer chains. These exposed amino groups have a positive (also known as cationic) charge in water or dilute acid. When 50% or more of the amino groups have been exposed the material becomes soluble in water or dilute acid due to the repulsion of the charged groups along the polymer chain. Thus, chitosan is defined as a derivative of chitin in which 50% or more of the amino groups are exposed or the chemical term is deacetlylated.

Starch is produced by all green plants and is stored for future energy use by the plant in their leaves, roots, and seeds. Commercial raw starch is obtained from corn, potato, rice, wheat and other seed or tuber crops. The raw starch is insoluble in water and is not efficacious as a hemostatic agent. Raw starch must be modified to increase its hydrophilicity. The modification process may be completely physical, chemical or a combination of the two. In general, raw starch is treated with water and heat to swell the raw starch granules and convert the material to a gelatinous mass. Further physical treatment such as extrusion or roll processing can be used to increase the hydrophilicity. After heating the raw starch with a measured amount of water, starch granules swell to a pasty substance, regularly arranged micelles of starch are broken, crystallites disappear, and the resulting composition is easily degraded by amylase. The pre-gelatinized starch is able to swell and/or dissolve in cold or room temperature water and form an adhesive paste whose tendency for retrogradation is lower than that of raw starch, affording easier handling during the production process.

The present technology uses water dispersible or water-soluble starch. Where the term starch is used with reference to the starch coatings according to the present technology the term starch is defined and limited to water-soluble, water-dispersible and/or gelatinized starches as known in the art. The modified starch may be either physically and/or chemically modified as described herein.

Gelatinized Starch Further Modified by Chemical Treatment.

Physically modified starch, for example, a pre-gelatinized starch treated solely with spray drying or irradiation process, is remarkably safe as a bio-absorbable, hemostatic material since it is not treated with any chemical agents and is readily degraded by enzymes present in the tissues.

Chemical modification of the starch polymer chains can further enhance the hydrophilicity of the gelatinized starch. The hydroxyl groups on the glucose monomers of starch can be reacted with a wide variety of chemical agents in order to introduce chemical functionality that can significantly increase the attraction of the starch for water. It has been found that introduction of carboxymethyl, hydroxyethyl or hydroxypropyl groups are particularly useful. Other useful modifications include phosphate esterification, and cross-linking using bifunctional agents such as epichlorohydrin. A complete discussion of the many possible modified starches useful as hemostatic agents is found in U.S. Pat. No. 8,575,132 (Ji).

When applied to a bleeding wound, the hemostatic efficacy of a particular starch composition is affected by both the water absorption characteristics (hydrophilicity) and the viscosity of the resulting starch-blood composition. The hemostatic properties of a particular modified starch depend upon, first, the characteristics of the raw starch, such as molecular weight of the starch polymers, and the relative amounts of amylose and amylopectin in the raw starch; and, second, modifications made to the particular starch by chemical treatments such as carboxymethylation or hydroxymethylation. U.S. Pat. No. 8,575,132 provides a useful discussion of the parameters found useful in preparing hemostatic starch compositions. In particular, a molecular weight range of 15,000 to 2,000,000 Daltons, a water absorption capacity ranging from greater than one gram of water per gram of modified starch to 500 grams of water per gram of modified starch, and inclusion of at least one carboxymethyl starch or one hydroxymethyl starch were found useful in preparing efficacious hemostatic compositions. These compositions, when contacting blood, produce a "starch-blood coagulation matrix" that has strong adhesive characteristics which can seal wounded tissue and stop bleeding. In addition, the interaction between the formed blood coagulation matrix and the functional groups of tissue proteins causes the "starch-blood coagulation matrix" to adhere to and seal the wounded tissue, resulting in hemostasis.

Other biocompatible hemostatic materials that may be added to the modified starches can comprise one or more of the groups of gelatin, collagen, carboxymethyl cellulose, oxidized cellulose, oxidized regenerated cellulose, and chitosan. The weight ratio between the modified starch and any other biocompatible hemostatic materials preferably is: 95:5, 90:10, 85:15, 80:20, 75:25, 70:30, 65:35, 60:40, 55:45, 50:50, 45:55, 40:60, 35:65, 30:70. This additional coagulant material may be added to the described modified starch hemostatic material before or during the vacuum freeze drying production process to produce a composite hemostatic composite. The production process may involve, but is not limited to, pre-mixing the coagulant material with the modified starch directly before any vacuum freeze drying process. The coagulant of the present invention comprises one or more combinations of the following group of blood coagulation factors: thrombin, fibrinogen, or calcium salts. The topical application of the layer of chitosan and modified starch can be used as a hemostatic agent to manage and control bleeding wound surfaces in humans, mammals, birds, or reptiles. Another advantage of the class of modified starch hemostatic material described herein is the rapid particle dispersion/dissolution in water, facilitating both the easy deposition of the starch onto the chitosan fabric material and the easy removal of excess modified starch particles from the wound by simple saline irrigation. The residual modified starch not actively involved in hemostasis can be rinsed away by irrigation. In the treatment of battle wounds, self rescue, or first aid, the hemostatic material remaining in small amounts will be absorbed by the body and the irritation of wound debridement or gauze removal is avoided.

The chitosan/modified starch hemostatic material has properties of stability, extended shelf life, resistance to high and low pressure, resistance to high temperatures up to 60 C and low temperatures down to −40° C., convenient storage, and physical stability. Therefore, it may also be employed as a hemostatic material for the military, emergency, and first-aid uses. Particularly, it can be adapted for extreme environmental conditions such as desert areas, polar regions, alpine areas, outer space, and underwater probes.

The chitosan/modified starch compositions are pliable and flexible. Therefore, they can be conformed to r wound surfaces with various shapes, sizes, and features, such as deep and irregular traumatic wounds. The chitosan/modified starch compositions contemplated here are easily sterilized using gamma irradiation, ultraviolet radiation, oxirane or ozone sterilization. Chemical treatments and addition of chemicals and elements (e.g., organic antimicrobials iodine, cupric ion, silver particles, etc.) may further sterilize or may retain antimicrobial activity of the coated material. Such additions may be made during or after manufacture of the structure.

One example of a production process for a biocompatible modified starch material useful in the present invention, comprising the steps of: First, providing a modified hygroscopic biocompatible starch material and loading it into an agglomerating apparatus under 40~50° C.; and Second, adding distilled water and producing a modified starch finished product material by particle agglomerating and pellet processing. The modified starch finished product material has a molecular weight over 15,000 Daltons (for instance, 15,000 To about 2,000,000 Daltons) and a grain diameter of 10-1000 μm, wherein starch grains with diameters of 30-500 μm represent no less than 95% of the total amount of starch grains. The modified starch material according to the present invention can be applied as a suspension in water or other solvents or as adry powder to a preformed layer of chitosan, which may or may not already be self-supporting. The layer may be made self-supporting by the coalescing of the aqueous (or organic solution such as alcoholic) solution or dispersion of the starch onto at least one surface of the chitosan layer. The chitosan/modified starch layer according to the present invention can be used on soft tissue and organs to rapidly and effectively control bleeding.

As noted herein, the chitosan/modified starch layer may be provided in a structure having additional layers associated into a final structure. For example, on multi-layer structure contemplated is
1) A multilayer pad;
2) Exterior layer has fabric of chitosan/modified starch fabric;
3) Optionally separated by freeze dried starch sheet;
4) At least one exterior chitosan fabric layers (as many as three) and separate internal starch layers as carrier layers bound to chitosan layers.
5) An optional support layer comprised of a polymeric or similarly elastic material. An example is polypropylene, polyurethane, polytetrafluoroethylene, or silicone A preferred structure as enabled above would have the fiber layer composition formed from chitosan fibers which are insoluble in water and starch particles which are soluble, or mostly soluble in water. The chitosan fibers are preferably 10 to 20 micrometers in diameter. The starch material (which is commercially available from Starch Medical, Inc.) is comprised mostly of carboxymethyl starch and is soluble and/or swellable in water. There is preferably no intentional cross-linking of either chitosan or starch.

An underlying concept of one aspect of the present technology is to combine the chitosan fibers, which exert a hemostatic effect by virtue of a positive charge on the fiber surface interacting with the negative charge on the surface of red blood cells and platelets, with a starch-based hemostat to get a synergistic effect. The combination products show better results than either product alone.

The chitosan fibers and the starch powder could be combined as a dry mix (and preferably exposed to moisture to assure securing the modified starch to the chitosan fibers) and some tests show that this will work. It is preferred to make a stable, reproducible formulation by coating the chitosan fibers with a solution/suspension of starch and drying the composite.

The chitosan layer (having the fibers bound or loosely associated) then has the at least one-side coating of the modified starch applied as by dip-coating, roller coating, spray coating, meniscus coating, slot coating, brush coating or the like. The gradation and depth of penetration of the applied modified starch liquid composition is controlled by viscosity, density, concentration and properties of the solution in combination with the particular coating techniques and rate and volume of application of the composition, as well as drying and pressure application parameters.

Water-soluble starches may be provided according to numerous technologies and sources, including at least U.S. Pat. No. 4,076,663 (Masuda) in which a highly water-absorbent resin is produced by polymerizing (A) starch or cellulose, (B) at least one monomer having a polymerizable double bond which is water-soluble or becomes water-soluble by hydrolysis and (C) a crosslinking agent, and subjecting, if necessary, the resulting product to hydrolysis; U.S. Pat. No. 6,833,488 describing a bio-compatible, bio-degradable macromolecular water-absorbent polymeric material having a three-dimensional configuration with intermolecular covalent bonds and containing free functional groups selected from OH, SH, $NH_2$, and COOH. The polymer is formed by polymer-polymer inter-coupling interaction between a natural water-soluble polymer A or its derivatives having a molecular weight between 20,000 and 500,000 Da, and a synthetic polymer B in a ratio of A:B of 15:85 to 85:15; U.S. Pat. No. 8,710,212 Thibodeau describing an absorbent material consisting of a molecular network of starch molecules, the starch molecules comprising an amylopectin content of at least 90% (w/w). The molecular network can either be comprised of self-entangled starches or cross-linked starches;

Description of Chitosan and Chitosan-STF

U.S. Pat. No. 8,703,176 (Zhu) describes a unique and proprietary chitosan structure and formulation. The structure is a nonwoven fleece made from high molecular weight chitosan fibers that offers a significant improvement in hemostasis performance and reliability. This material provides a strong technology platform that can be used to create a family of products each with its own indications for use. Commercial hemostatic products using this technology are produced by Chitogen Inc.

Chitosan is a polymer, soluble in water or dilute acid, made from chitin by chemical treatment. Chitin is an abundant natural product that is the primary structural material in the shells of shrimp, lobsters and other crustaceans. Chitin's structural role in shells is similar to the role of CHEMICAL STRUCTURES OF CELLULOSE (Image a) AND CHITIN AND CHITOSAN (Image b)

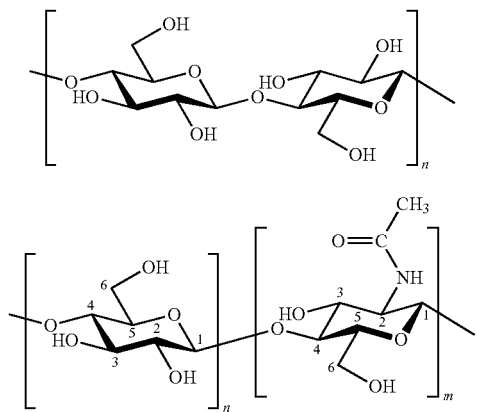

cellulose in plants. Both chitin and cellulose are high molecular weight polymers containing glucose molecules linked together to form long, linear polysaccharide chains.

Chitin is recovered from the crab shell by treatment with acid to remove the minerals followed by treatment with alkali to remove protein. After these treatments, purified chitin remains as thin, white sheets that are further processed into chitosan. Chitosan is made by heating purified chitin with strong alkali (40% sodium hydroxide) to remove some of the acetyl groups from the polymer chains. These exposed amino groups have a positive (also known as cationic) charge in water or dilute acid. When 50% or more of the amino groups have been exposed the material becomes soluble in water or dilute acid due to the repulsion of the charged groups along the polymer chain. Thus, chitosan is defined as a derivative of chitin in which 50% or more of the amino groups are exposed or the chemical term is deacetlyated.

Hemostatic products made from chitosan (SoftSeal®-STF, Chitogen Inc) are non-woven pads composed of chitosan fibers attached to a thin polypropylene backing material. The pad is intended to be used as an aid in the management of topical bleeding wounds such as vascular access sites and topical lacerations.

The principle of operation of chitosan-based products is believed to result from bioadhesion between the chitosan polymer chains (positive charge) and blood and tissue components (negative charge) as well as pressure related tamponade. The charge density and uniformity of the positive charge is enhanced by the surface treated fiber (STF) process as described by U.S. Pat. No. 8,575,132.

Example, Description of Duplex Formulation

Chitosan fibers (Soft-Seal-STF, Chitogen Inc) were coated with carboxymethyl starch (AMP-66, Starch Medical) using an airless spray technology and the resulting duplex structures were evaluated using a recognized animal bleeding model.

Chitosan fibers were spray-coated with two levels of modified starch. Carboxymethyl starch, 5.0 or 10 grams was dissolved in 600 ml of 5% acetic acid. The spray coating was done by hand control using a spray painter (home use) held approximately 12 inches from the fabric which was placed on a paper background. The sprayer was activated for a total of three passes and total exposure time was approximately 2 to 3 seconds. The sprayed chitosan fibers were air-dried overnight and placed into a zip-lock bag. No evidence of leakage from the sprayed material was observed.

The ability of the two prototypes to control bleeding and their adherence to the bleeding surface was assessed. These studies investigated the rapid control of bleeding using a hold or compression times of 1 minute or 2 minutes used to determine hemostatic performance from the bleeding soft organ.

In both the 5 and 10 gram starch solutions, coated fibers were observed on the surface of the fiber mat with uncoated fibers in the depths of the mat.

FIG. 5 is a schematic representation a cutaway side view of the chitosan fiber matrix 100 similar to that seen in FIGS. 3A and 3B emphasizing distribution of the AMP layer 106a from one surface 102 into the non-woven chitosan 104. Remembering that this FIG. 5 is an illustrative rendition and is not intended to be a limiting description of distribution of materials, thicknesses and rheology of layers, it can be seen that in Zone 1, there is a heavier thickness 106 of the starch coating 106a. In Zone 2, there is a thinner coating 108 of the starch coating 106a. In Zone 3, there tends to be a more discontinuous coating 110 of the starch coating 106a. In Zone 4, there is essentially no starch coating 106a in this rendition. There are open volumes 112 between the coated 106a chitosan fibrous elements 104 within the matrix 100. The distribution is illustrative of how materials are likely to be distributed from a single side (through surface 102) application of the starch coating 106a. Different methods of application (e.g., two-side application, dipping, pressure-coating, spray coating, meniscus coating and the like) will create varying patterns if starch distribution within the matrix 100. For example, with two side coating application of the starch, a complete cross-section distribution might look more like a mirror image of Zone 1, Zone 2, Zone 2 again and Zone 1 again (in order) so that there is a relatively continuous, though varying in thickness, coating of starch across the entire thickness of the matrix. It might also be possible to have mirror cross-sections of a) Zone 1, Zone 2, Zone 3m Zone 2, Zone 1, or b) Zone 1, Zone 2, Zone 3, Zone 4, Zone 3, Zone 2 and Zone 1, Not only the thickness of the starch coating 106 may vary across the thickness of the fabric, but also the coating weight per volume will vary and the coating weight variations (in a two-side coated matrix) may be different from one surface versus the other surface, Animal Test Results Experiment #1

The soft organs of a live pig were selected for a bleeding model to test the efficacy of the preparations. A 6 mm biopsy punch that was inserted to a depth of approximately 6 mm to create circular incisions in both the liver and spleen of the pig. The test material was applied and held for one minute for liver incisions and two minutes for splenic incisions. The bleeding model is described in detail in the protocol is XVE004, from American Preclinical Services, Minneapolis, Minn. The duplex formulations of chitosan fiber and modified starch at the 5 gram and 10 gram level showed superior performance to the chitosan fiber control. There was less bleed through at the 1 minute hold for the liver and 2 minute hold for the spleen. It was determined that the 1 minute hold although adequate for the liver was insufficient for the spleen.

This bleeding model was a very severe test for hemostatic pads. A hold time of one or two minutes although useful for the animal model is not specifically intended to predict use in clinical situations.

In this particular study, we observed an improvement in hemostatic performance for the 10 gram material when compared to the lower concentration, 5 grams. However both were an improvement compared to the plain STF and thus the three concentrations (zero, 0.8% and 1.7% grams/ml) provide a clear dose response trend.

The chitosan fiber/modified starch composition was folded over to provide a double thickness layer. This configuration was also tested in the more demanding spleen bleeding sites and was found to be very effective. In contrast, the control chitosan fiber pad alone when doubled up did not achieve an improved hemostatic control.

These experiments show that a single layer of chitosan fibers, coated with modified starch provide an improved hemostatic pad for topical, percutaneous injury. For more severe bleeding, the use of multiple layers is preferred.

Experiment #2

Using the same materials and method as used for Example 1, a new set of starch fiber pads coated with modified starch was prepared The pads were tested in the same animal bleeding model.

Light microscope and scanning electron microscope images are shown in Figure YYY Wounds treated with pads of chitosan fibers coated with modified starch oozed less than the chitosan fiber pads alone. Oozing is defined as blood leaking from the edge of the wound after the pad is applied and held in place for one or two minutes. Such oozing is considered a failure to control the bleeding from the wound.

Using the liver and the spleen we tested 19 chitosan fiber pads (control) and 18 pads of chitosan fiber coated with modified starch. Both groups exhibited good hemostatic performance but for the control pads there were 4 that oozed (failed). That is 4/19=21% showed some blood leakage. For the chitosan fibers coated with modified starch there were no failures. Using Fisher's Exact Test to compare these results we calculate that the probability of these results being due to chance is 0.056.

What is claimed:

1. An absorbent layer comprising a non-woven fabric layer of water-insoluble chitosan fibers having a continuous coating of water-absorbent starch on at least one face of the fabric layer, wherein the starch has been modified to include hydrophilic groups into or onto molecular chains of the starch.

2. The layer of claim 1 wherein the coating of water-absorbent starch penetrates into the fabric layer from a first surface as a continuous coating over the chitosan fibers to a depth of at least 25% of the fabric layer of chitosan fibers.

3. The layer of claim 2 wherein the chitosan fibers have average diameters of from 8 to 25 micrometers and the water-absorbent starch comprises carboxymethyl starch.

4. The layer of claim 2 wherein the starch has been modified to include hydrophilic groups into or onto molecular chains of the starch to form a biocompatible starch that promotes hemostasis.

5. The layer of claim 2 carried on a structural support secured to the second surface of the layer.

6. A method of mediating blood flow from a wound by applying the first surface of a layer according to claim 2 against the wound from which blood is flowing and clotting blood from the wound.

7. The layer of claim 1 wherein the chitosan fibers have average diameters of from 5 to 30 micrometers and the starch has been chemically modified to include hydrophilic groups onto the molecular chains of the starch.

8. The layer of claim 1 wherein the chitosan fibers have average diameters of from 8 to 25 micrometers and the starch has been chemically modified to include hydrophilic groups into the molecular chains of the starch.

9. The layer of claim 8 wherein the coating of water-absorbent starch penetrates from a first surface into the fabric layer over the chitosan fibers to a depth of at least 50% of the fabric layer of chitosan fibers towards a second surface of the layer and wherein there is a grading of average weight of starch/chitosan in which the average weight of starch/cellulose decreases from the first surface from which the starch has penetrated into the fabric to the depth of at least 50%.

10. The layer of claim 9 wherein average weight of starch/chitosan decreases from one surface from which the starch has penetrated into the fabric to the depth of at least 50% of the fabric layer as a result of applying the layer of water-absorbent starch by dip-coating, roller coating, spray coating, meniscus coating, slot coating or brush coating of a solutions of the water-absorbent starch onto the non-woven fabric layer consisting essentially of chitosan.

11. The layer of claim 10 wherein the starch has been modified to include hydrophilic groups into or onto molecular chains of the starch to form a biocompatible starch that promotes hemostasis.

12. The layer of claim 9 wherein the starch has been modified to include hydrophilic groups into or onto molecular chains of the starch to form a biocompatible starch that promotes hemostasis.

13. The layer of claim 12 carried on a structural support secured to the second surface of the layer.

14. A method of mediating blood flow from a wound by applying the first surface of a layer according to claim 9 against the wound from which blood is flowing and clotting blood from the wound.

15. A method of mediating blood flow from a wound by applying the first surface of a layer according to claim 8 against the wound from which blood is flowing and clotting blood from the wound.

16. The layer of claim 1 wherein the chitosan fibers have average diameters of from 10 to 20 micrometers.

17. The layer of claim 1 wherein the coating of water-absorbent starch penetrates from a first surface into the fabric layer over the chitosan fibers to a depth of at least 50% of the fabric layer of chitosan fibers towards a second surface of the layer and wherein there is a grading of average weight of starch/chitosan in which the average weight of starch/cellulose decreases from the first surface from which the starch has penetrated into the fabric to the depth of at least 50%.

18. The layer of claim 17 wherein average weight of starch/chitosan decreases from the first surface from which the starch has penetrated into the fabric to the depth of at least 50% of the fabric layer and wherein there is a grading of average weight of starch/chitosan in which the average weight of starch/cellulose decreases from the first surface from which the starch has penetrated into the fabric to the depth of at least 50%.

19. The layer of claim 17 wherein the starch has been modified to include hydrophilic groups into or onto molecular chains of the starch to form a biocompatible starch that promotes hemostasis.

20. The layer of claim 17 carried on a structural support secured to the second surface of the layer.

21. A method of mediating blood flow from a wound by applying the first surface of a layer according to claim 17 against the wound from which blood is flowing and clotting blood from the wound.

22. The layer of claim 1 carried on a structural support secured to the second surface of the layer.

23. A method of mediating blood flow from a wound by applying the first surface of a layer according to claim 1 against the wound from which blood is flowing and clotting blood from the wound.

24. A method of mediating blood flow from a wound by applying the layer according to claim 1 against the wound from which blood is flowing and clotting blood from the wound.

25. The absorbent layer of claim 1 wherein the water-absorbent starch coating is translucent to white light.

26. The absorbent layer of claim 1 wherein the water-absorbent starch coating is transparent to white light.

\* \* \* \* \*